United States Patent [19]

Zaiger et al.

[11] Patent Number: Plant 7,198

[45] Date of Patent: Mar. 20, 1990

[54] APRICOT TREE EARLICOT

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 334,222

[22] Filed: Apr. 5, 1989

[51] Int. Cl.[4] ..... A01H 5/00

[52] U.S. Cl. ..... Plt./39

[58] Field of Search ..... Plt./39

*Primary Examiner*—James R. Feyrer

[57] ABSTRACT

A new and distinct variety of apricot tree which has the following unique combination of outstanding features that are desirable in a new variety:

1. Early maturing fruit.
2. Fruit with good flavor and eating quality.
3. Fruit with firm flesh, good handling and shipping quality.
4. Heavy and regular production.
5. Relatively uniform ripening of fruit throughout the tree.

1 Drawing Sheet

ORIGIN OF THE VARIETY

The present variety of apricot tree was developed in the experimental orchard located near Modesto, Calif., as a cross between two selected apricot seedlings with the identification numbers of 2W42 and 8W17. The seedling 2W42 which was the female parent, originated from a group of open pollinated seedlings of Flaming Gold Apricot (U.S. Plant Pat. No. 2,822). The pollen parent 8W17 originated from a group of open pollinated Perfection Apricot (non-patented) seedlings. We grew and maintained these first generation seedlings under close observations, one such early maturing seedling, having especially desirable fruit characteristics was selected for reproduction and commercialization.

ASEXUAL REPRODUCTION OF THE VARIETY

Asexual reproduction of the new variety of Apricot tree by budding was preformed in the experimental orchard located near Modesto, Calif. and show that said characteristics run true to the original tree and are established and transmitted through succeeding propagations.

SUMMARY OF THE VARIETY

A new and distinct variety of apricot tree which is of large size, vigorous, upright growth, and a regular and productive bearer of early maturing, firm, large, freestone fruit with good flavor and eating quality, characterized to its novelty by its uniform size and maturity throughout the tree. In comparison to Flaming Gold Apricot (U.S. Plant Pat. No. 2,822), the fruit of the present variety matures approximately eight days earlier, has firmer flesh with greater handling and shipping quality.

BRIEF DESCRIPTION OF THE PHOTOGRAPHS

The accompanying photographs show typical specimens of the foliage and fruit of the new variety, the upper and lower surface of the leaves being illustrated with an exterior and sectional view of the fruit, with a fruit being divided in its suture plane to reveal flesh coloration and showing a stone remaining in place. The photographic illustrations were taken shortly after being picked at maturity (shipping ripe) and the colors are as nearly true as is reasonably possible in a color representation of this type.

DESCRIPTION OF THE VARIETY

The following is a botanical detailed description of the new and distinct variety of apricot tree, its flowers, fruit and foliage, bases on observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Production.*—Productive.
- Bearer.—Regular.

Trunk:
- *Size.*—Large.
- *Texture.*—Shaggy.
- *Color.*—Brown to grayish brown.

Branches:
- *Size.*—Medium.
- *Texture.*—Medium rough.
- *Color.*—New growth — reddish brown. Old growth — brown to grayish brown.

Leaves:
- *Size.*—Medium to large. Average length — $3\frac{1}{4}''$. Average width — 3″.
- *Form.*—Ovate.
- *Thickness.*—Medium.
- *Petiole.*—Average length — $1\frac{3}{8}''$. Average width — 1/16″.
- *Glands.*—Size — small. Average number 1, range 0–3. Primarily on base of leaf blade.
- *Color.*—Upper surface — green (29-E-8) to (29-F-8). Lower surface — grayish green (29-E-6) to (29-E-7).

Flower buds:
- *Size.*—Medium to large.
- *Length.*—Medium.
- *Form.*—Plump.

Flowers:
- *Size.*—Large.

*Blooming period.*—Date of first bloom: Feb. 23, 1985. Date of last bloom: Mar. 2, 1985. Varies slightly with climatic conditions.

*Pollen.*—Present.

*Color.*—Varies from white to light pink.

Fruit:

*Maturity when described.*—Firm Pipe.

*Date of first picking.*—May 20, 1985.

*Date of last picking.*—May 25, 1985.

*Size.*—Average diameter axially — $1\frac{3}{4}''$ to $2\frac{3}{8}''$. Transverse diameter in suture plane — $1\frac{3}{4}''$ to $2\frac{1}{2}''$. Diameter measured at right angles to suture plane — $1\frac{3}{4}''$ to $2\frac{1}{2}''$.

*Form.*—Globose — slightly variable. Slight flattened at stem and apex. Some fruit slightly compressed at suture.

*Suture.*—Usually pronounced. Extends from base to apex.

*Base.*—Retuse.

*Apex.*—Slightly retuse.

*Cavity.*—Rounded to slightly elongated in suture plane. Average depth — $\frac{1}{4}''$ to 3/16". Average breath —$\frac{1}{2}''$.

Skin:

*Thickness.*—Medium to thin.

*Texture.*—Medium.

*Tendency to crack.*—Slight.

*Down.*—Scant, very short.

*Color.*—Light orange ground color (6-B-7) to (7-B-7). Blush — orange red (9-B-7) to (10-B-7).

Flesh:

*Ripens.*—Fairly uniform, only very slightly later at base.

*Texture.*—Firm.

*Flavor.*—Mild: predominantly apricot.

*Eating quality.*—Good.

*Color.*—Light orange (6-B-5) to (6-B-7).

Stone:

*Type.*—Freestone.

*Size.*—Medium to large. Average length — $1\frac{5}{8}''$ to $1\frac{1}{4}''$. Average breadth — $\frac{3}{4}''$ to $\frac{7}{8}''$. Average thickness —$\frac{1}{2}''$ to $\frac{5}{8}''$.

*Form.*—Ovid.

*Base.*—Straight.

*Apex.*—Nearly rounded, only slight pistol point.

*Surface.*—Irregularly pitted throughout.

*Ridges.*—Slight ridges extending across the surface of the stone on both sides of the suture plane.

*Tendency to split.*—None.

*Color.*—Light brown to brown (6-D-5) to (6-E-6).

Use: Dessert.

*Market.*—Local and long distance.

Keeping quality: Good.

Shipping quality: Good.

The apricot tree and its fruit herein described may vary in slight detail due to climatic, soil conditions and cultural practices under which the variety may be grown; the present variety is that of the variety grown in the experimental orchard under the ecological conditions prevailing at Modesto, Calif.

We claim:

1. A new and distinct variety of apricot tree substantially as illustrated and described, characterized by its large size, vigorous, upright growth and a productive and regular bearer of large, firm, freestone fruit with good flavor and eating quality; the new variety is further characterized in comparison to Flaming Gold Apricot (U.S. Plant Pat. No. 2,822) by maturing approximately 8 days earlier, having firmer flesh with greater handling and shipping quality.

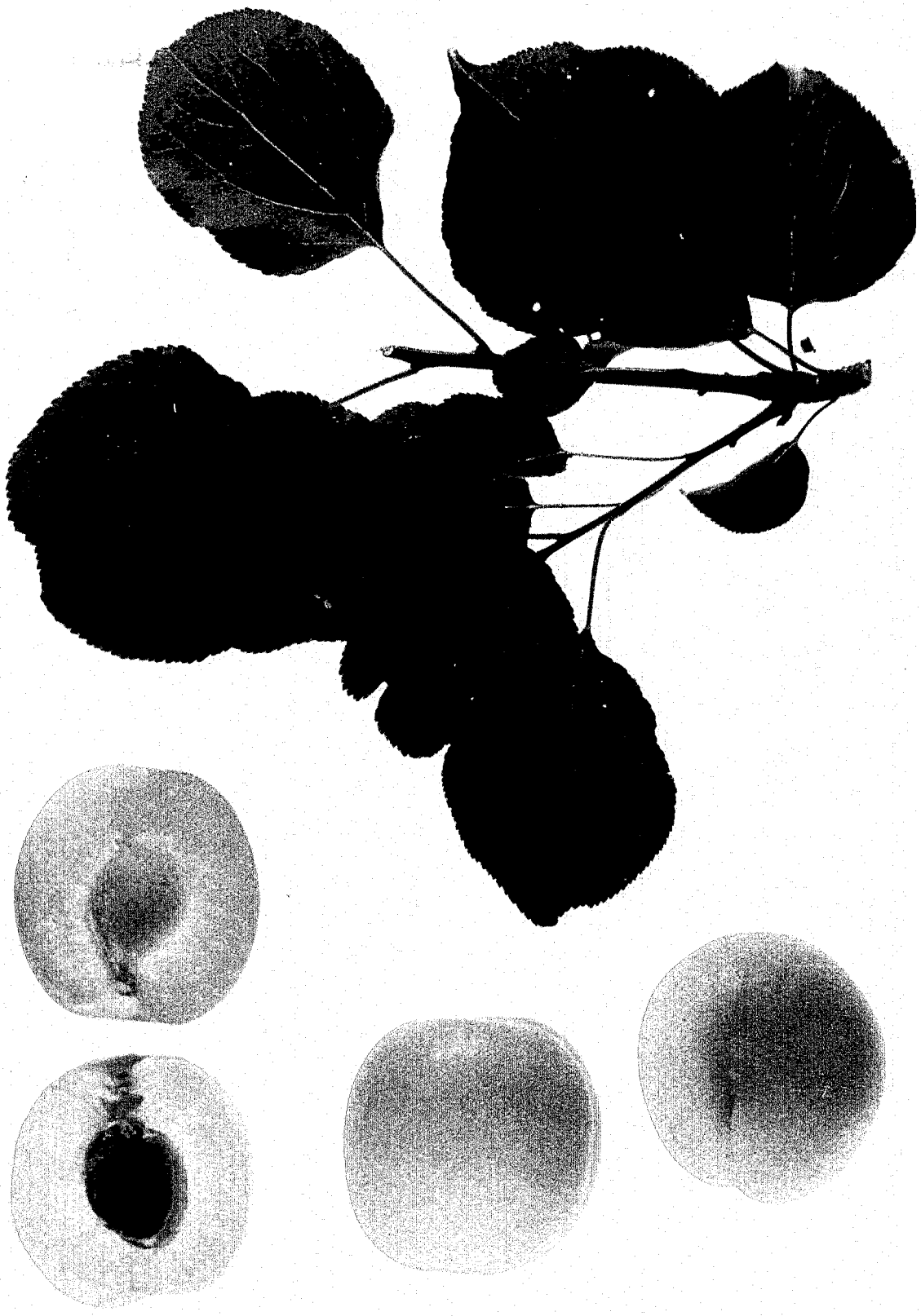

* * * * *